(12) United States Patent
Cohen et al.

(10) Patent No.: US 6,558,665 B1
(45) Date of Patent: May 6, 2003

(54) ENCAPSULATING PARTICLES WITH COATINGS THAT CONFORM TO SIZE AND SHAPE OF THE PARTICLES

(75) Inventors: Itai Cohen, Chicago, IL (US); Sidney Nagel, Chicago, IL (US); Horacio Rilo, Chicago, IL (US); Milan Mrksich, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/575,844

(22) Filed: May 18, 2000

Related U.S. Application Data

(60) Provisional application No. 60/134,612, filed on May 18, 1999.

(51) Int. Cl.[7] .......................... A01N 65/00; C12N 11/02; C12N 11/10; C12N 11/08; C12N 5/00
(52) U.S. Cl. ...................... 424/93.7; 435/177; 435/178; 435/180; 435/382
(58) Field of Search ................................ 435/174, 177, 435/178, 180, 382; 424/93.7

(56) References Cited

U.S. PATENT DOCUMENTS

| | | | |
|---|---|---|---|
| 4,391,909 A | * | 7/1983 | Lim ........................... 435/178 |
| 5,871,767 A | * | 2/1999 | Dionne et al. ............... 424/422 |
| 5,900,160 A | * | 5/1999 | Witesides et al. ............. 216/41 |

* cited by examiner

*Primary Examiner*—David M. Naff
(74) *Attorney, Agent, or Firm*—Brinks Hofer Gilson & Lione

(57) ABSTRACT

Particles such as islet cells are encapsulated by a method that forms a coating of uniform thickness that conforms to the size and shape of the particles. Two substantially immiscible liquids of different densities are provided in a container as upper and lower liquids such that an interface exists between the liquids. The upper liquid is less dense and has a greater viscosity than the lower liquid which is a coating liquid containing particles to be encapsulated. A tube is positioned in the upper liquid such that an orifice of the tube is above the interface. A pump connected to the tube sucks liquid through the tube at a rate sufficient to form a spout containing substantially the lower liquid extending between the interface and the tube orifice. The spout has maximum diameter at the interface and decreases in diameter as the spout approaches the tube orifice. Particles in the lower liquid are drawn up through the spout as liquid is withdrawn, and coated particles are released from the spout at a point where the diameter of the spout is less than the diameter of the particles, and the coated particles flow through the tube. The coating liquid may be a pre-polymer that can be polymerized and crosslinked after coating. The coated particles have therapeutic applications such as administering coated islet cells to treat diabetes.

20 Claims, 4 Drawing Sheets

ENCAPSULATING PARTICLES WITH COATINGS THAT CONFORM TO SIZE AND SHAPE OF THE PARTICLES

PRIORITY INFORMATION

This non-provisional application claims priority to U.S. Provisional Application No. 60/134,612, filed May 18, 1999, incorporated herein by reference in its entirety.

GOVERNMENTAL RIGHTS

The United States government has rights in the present invention pursuant to grant number DMR-9722646 from NSF, internal number 5-28354 from DARPA, grant number 1-RO3-DK54868-01 from NIH, grant number DMR-9400379(MRSEC) from NSF, and grant number DE FG02-92ER25119 from DOE.

BACKGROUND OF THE INVENTION

The present invention relates to a method for encapsulating particles, and more particularly, to a method for encapsulating particles with a coating that substantially conforms to the size and shape of an individual particle utilizing selective withdrawal technology. The invention also includes specific uses for the particles encapsulated according to the inventive method.

Selective withdrawal technology involves the "selective" withdrawal of the upper fluid, or both fluids, from a container holding two fluids of different densities. In most cases, this technology has been applied to combinations of fluids where the upper fluid is a gas, such as air, and the lower fluid is a liquid. Examples of such use of this technology are found in the oil industry.

When two fluids of different densities are added to a container, the less dense fluid floats on top of the fluid having a greater density, and an interface exists between the fluids. If it is desired to controllably withdraw the upper fluid only, or a combination of both fluids, a tube connected to a suction pump may be inserted into the upper fluid to suck up fluid from the vicinity of the orifice of the tube. At a low suction level, a slow flow of the less dense upper fluid layer enters the nozzle of the tube, and the more dense fluid remains in the container. The low level of suction generally causes a portion of the interface between the fluids to deform upwardly from its horizontal orientation to form a small hump in the area below the nozzle. Under these low suction conditions, the hump remains stable, and all of the withdrawn fluid comes from the upper layer.

If, however, the suction level is sufficiently increased, the hump becomes unstable and forms a spout at the interface of the two fluids. The spout comprises the heavier, lower layer, which is entrained in the lighter, upper layer. When a spout is formed, portions of the heavier fluid also enter the tube. The diameter of the spout decreases substantially from its base toward the tube orifice. Further increasing the suction level widens the spout. Once inside the tube, the spout breaks up into small droplets.

When applying this technology to combinations of fluids in which the upper fluid is air, the system is generally unstable. The spout is not stationary, and it often meanders and breaks apart in a disordered pattern. This lack of stability of the spout has hindered more widespread use of the selective withdrawal technology, since the instability makes it difficult to design processes that have an acceptable level of predictability and reproducibility. If more controllable use of this technology could be developed, the selective withdrawal technology could be put to more and better productive uses.

SUMMARY OF THE INVENTION

The present inventors have addressed the problems of the prior art by developing a selective withdrawal system in which the spout formed by the withdrawal of the entrained fluid is substantially stationary. As a result, the spout does not meander in a disorderly manner as in the example discussed above when air was used as the upper (withdrawn) fluid. It has been determined that such fluctuations of the spout can be reduced dramatically when air is replaced as the upper fluid by a fluid, such as a viscous liquid, more capable of supporting a stationary spout. When such a fluid is utilized as the upper fluid in a selective withdrawal system, a clean, reproducible and substantially stationary spout may be formed.

Due to the reproducible nature of the results in such combinations, the technology may be applied to areas where greater predictability of the action is required, such as the encapsulation of particles. When utilizing the method of the present invention, coatings may be applied to particles of varying sizes and shapes that substantially conform to the respective size and shape of the particles. A conformal coating of this type may be used for various applications in which uniform coatings of multi-sized particles are desired, such as the encapsulation of cells for transplantation. One example of such potential use is the microencapsulation of islet cells with a polymeric coating for transplantation into diabetic patients. The particles may be encapsulated with a coating that permits the transfer through the coating of useful compounds, such as glucose, insulin and metabolites, while preventing the transfer of compounds that may cause harmful interaction with the immune system. Similar uses may be possible for treatment of other conditions, which treatments have heretofore been hindered by undesirable immunogenic responses.

Another use to which this technology may be applied is the coating of particles for use in systems, such as drug delivery systems, in which timed release of a drug or other coated substrate is desirable. In such applications, particles can be coated to a predetermined thickness with a particular compound, or alternatively, a predetermined number of coatings of predetermined thickness and composition can be applied to the substrate.

In addition to the foregoing uses, other possible uses are described hereinafter. It should be understood that the specific uses described are merely intended to be illustrative of some of the uses to which the technology of the present invention may be applied. Those skilled in the art will appreciate that the present invention will have application to additional uses, all of which are considered to be within the scope of the present invention.

DETAILED DESCRIPTION OF THE PREFERRED EMBODIMENTS

Figure 1A:
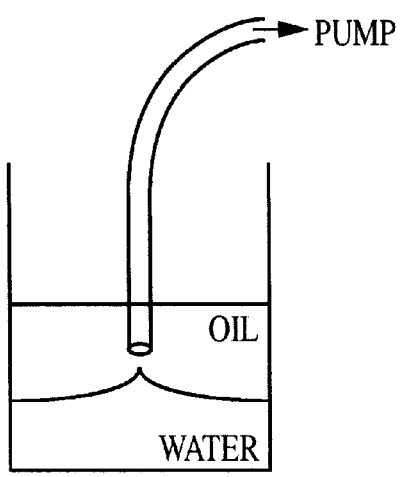
FIG. 1a illustrates a container including two fluids of different densities, with a tube inserted into the upper fluid according to a preferred embodiment of the present invention.

In order to apply selective withdrawal technology for productive uses, such as particle encapsulation, it is important that parameters be developed so that the results of the selective withdrawal operation are both predictable and reproducible. The present inventors have determined that such results may be obtained when the spout formed by the withdrawal of the entrained (spout-forming) fluid does not meander in a disorderly manner as in the example discussed above in which air was used as the upper fluid, but rather, is substantially stationary. When the spout is substantially stationary, sufficient controls can be applied to a system so that a controllable amount of a fluid may be selectively withdrawn.

When applying selective withdrawal technology to a particular use, some or all of the following parameters may be adjusted as desired to control the size and shape of the spout, and thereby optimize the particular application:

1) Density of the primary fluid being withdrawn;
2) Density of the entrained (spout-forming) fluid;
3) Viscosity of the primary fluid;
4) Viscosity of the entrained fluid;
5) Inner and outer diameter of the tube used to withdraw the fluids;
6) Height of the tube orifice from the unperturbed fluid-fluid interface;
7) The surface tension of the interface;
8) The flow rate of the fluid through the tube;
9) Capacity of the suction pump;
10) Size of container which holds the liquids;
11) Angular momentum of either or both fluids; and
12) Introduction of physical obstructions in the container. Obstructions, such as a conical bulge connected to the bottom of the container, alter the flow of the fluid by causing it to flow around the obstruction.

In most practical applications of this technology, the selective withdrawal operation will likely involve the insertion of a tube from above into the less dense, upper layer of a container containing two fluids, and the application of suction directly to the tube in the upper layer. In this case, the "primary" fluid is the upper, less dense fluid, and the "entrained" fluid is the lower, heavier fluid. Unless specifically stated to be otherwise, this preferred embodiment is the arrangement referred to in the examples and discussion provided herein.

Notwithstanding the foregoing, it should be noted that the reverse arrangement is also within the scope of the invention. In the reverse arrangement, the tube is inserted into the heavier, lower layer. This can be accomplished by inserting the tube through the bottom of the container, or alternatively, by inserting an L-shaped or other appropriately-shaped tube from above into the lower fluid. In the reverse arrangement, the "primary" fluid is the heavier, lower layer, and the "entrained" fluid is the less dense, upper layer. The suction is applied directly to the tube in the lower layer, causing the hump to be downwardly-directed, rather than upwardly-directed as in the previously-described arrangement. When the suction is increased to a sufficient level, a spout is formed comprising the lighter layer entrained in the heavier (lower) layer.

Particles coated according to the teachings of the present invention may comprise inorganic hardened substrates such as beads, organic particles such as pharmaceuticals or biological agents such as proteins, nucleic acids, or whole cells or viruses. Although the particles to be coated need not have the same size and shape, the method is limited to particles having a size and shape permitting them to be drawn into the tube by the suction created by the pump. However, the diameter of the suction tube, and the capacity of the pump, may be varied for a particular application; therefore, the adjustment of these parameters permits the inventive method to be applied to a very wide range of particle sizes and shapes.

The coating of particles by the inventive method is based upon the property of fluid motion that occurs when a lower fluid forms a spout as it is drawn upwardly by suction into a tube. The shape of the interface between the two fluids is such that particles in the lower fluid become entrained in the flow, and eventually cause a rupture in the spout. This action enables each particle to become selectively "shrink-wrapped" in a coating which conforms to the size and shape of the particle. Applying this technology enables coatings of various thickness, compositions, and number of layers to be applied to substrate particles. Thus, the technique is readily applicable to the coating of particles varying widely in size and shape.

In order to coat such particles, a container is provided having two (or more in some alternative embodiments) fluids of different densities. Although it is expected that the fluids will be substantially immiscible, the invention is not so limited. Rather, the invention may also be practiced with miscible fluids having different densities, so long as the fluids have not been mixed, and an interface exists between them. However, such systems utilizing miscible fluids are generally not as easily controlled as systems utilizing immiscible fluids; therefore the use of immiscible fluids is preferred. In addition, if miscible liquids are utilized, the operation must generally be carried out rapidly so that the fluids do not mix with each other prior to completion of the selective withdrawal operation.

The upper, less dense fluid floats atop the lower, more dense fluid in the container. A tube, connected to a suction pump, is inserted into the upper fluid. Generally, when coating particles in the 100–800 microns range, a capillary tube having an inner diameter of about 0.5 cm is sufficient. The height of the tube orifice above the fluid interface, and the pumping rate, are adjusted to levels such that the initial hump formed at the interface becomes unstable, and a spout is formed. For each tube height there is a unique flow rate at which the hump becomes unstable and forms a spout. The pump must be able to withdraw fluid through the tube at a constant flow rate in order to maintain the interface in dynamic equilibrium. If desired, the tube height and/or the flow rate can be varied to alter the shape of the spout. In most applications, the inner diameter of the tube should be of sufficient size such that the spout-forming fluid is drawn up the center of the tube, and does not directly contact the inner wall of the tube. Rather, in such instances, only the upper fluid directly contacts the tube. The spout is fully entrained in the upper fluid. As a result, the spout, which often may comprise a sticky or gummy polymeric fluid, is not permitted to adhere to or otherwise "gum up" the inner diameter of the tube.

Figure 1B:
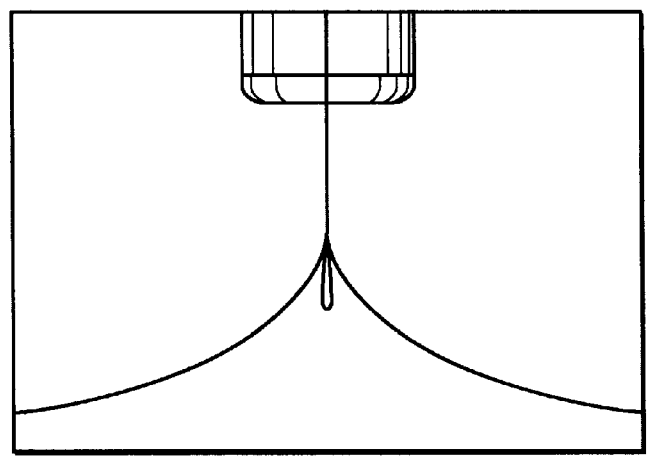
FIG. 1b is an optical micrograph showing a selective withdrawal operation in which a lower phase of water is drawn to a tube through an upper fluid of oil.

FIG. 1a illustrates a container including two fluids of different densities according to a preferred embodiment of the present invention. In this embodiment, a tube connected to a suction pump is inserted from above into the less dense upper fluid. FIG. 1b is an optical micrograph showing a selective withdrawal operation in which a lower phase of water is drawn through an upper fluid of oil. The pipette has a diameter of approximately one millimeter.

When the pump produces sufficient suction to form the spout, the particles enter the spout along with the entrained fluid. Normally, the degree of flow of the entrained fluid is such that only particles near the interface are sucked up into the spout. Thus, it is preferable to use particles that are less dense than the lower fluid, so that the particles float in the lower fluid at or near the interface of the upper and lower fluids, and do not sink to the bottom of the container.

As the particles are first drawn into the spout, they are completely surrounded by the entrained fluid of the spout, since the base of the spout has a much larger diameter than the diameter of any individual particle. However, the diameter of the spout decreases substantially as the spout approaches the orifice of the tube. Thus, as the pump draws the individual particles higher in the spout, a particle begins to occupy an increasingly larger fraction of the spout diameter. At some point during the journey of a particle through the spout, the diameter of the particle exceeds that of the spout, thereby deforming the interface of the spout with the upper fluid and causing the particle to extend radially outward from the smooth shape of the spout.

Figure 2C:
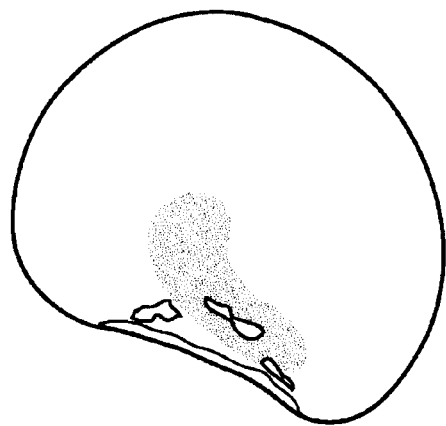
FIG. 2c is an enlarged optical micrograph showing a poppy seed coated with a PEG polymer according to the inventive method.
Figure 2B:
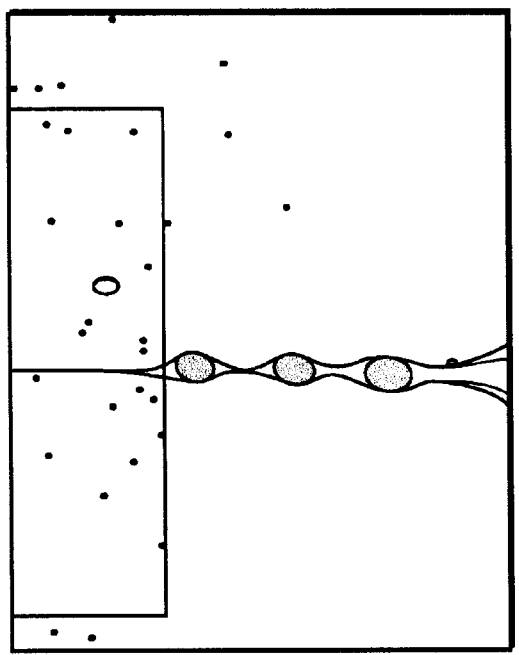
FIG. 2b is an optical micrograph showing three poppy seeds drawn sequentially upwardly in a spout.
Figure 2A:
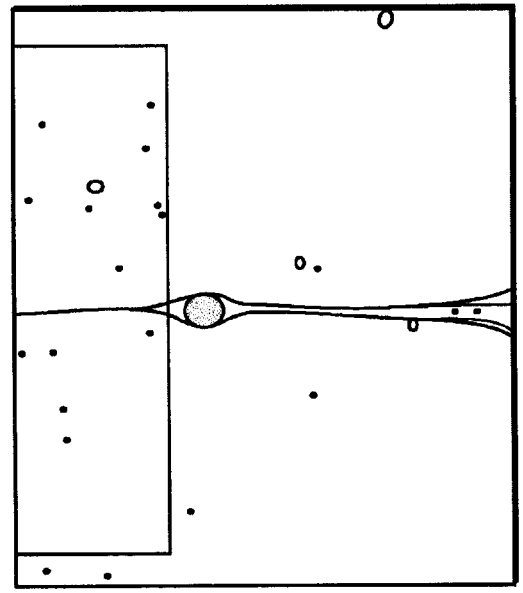
FIG. 2a is an optical micrograph illustrating a poppy seed as it is drawn upwardly into a tube via a spout.

FIG. 2a is an optical micrograph illustrating the coating of a poppy seed by selective withdrawal. Coating a poppy seed illustrates the utility of the inventive method in coating particles of irregular shape, which in this case comprises a generally kidney-shaped particle having a long dimension of approximately 800 microns. As shown in the figure, the single particle is trapped in the stream of a water/pre-polymer spout which is flowing through heavy mineral oil. As the particle rises in the spout, its diameter exceeds that of the spout, resulting in the break-up of the spout, and leaving a single particle surrounded by a substantially-uniform pre-polymer coat. FIG. 2c is an optical micrograph of a poppy seed coated by a PEG polymer in this manner, in which the PEG pre-polymer was polymerized by irradiating the particle by a broad band light source to obtain. The image shown in FIG. 2c demonstrates that the selective withdrawal operation can install a conformal polymer coating on irregularly-shaped particles.

The arrangement shown in FIG. 2a is energetically very expensive for the fluid interface, because it increases the surface area (and therefore the surface tension energies) over the otherwise smooth unperturbed shape of the spout. As a result, the spout breaks apart both above and below the particle, leaving a coating of (the lower) fluid completely surrounding the particle. A small tail of fluid remains connected to the particle both in front of and behind it. These tails are smoothed away by surface tension forces, thereby bringing the excess fluid into the rest of the coating. Since the break-up of the spout is initiated when a particle reaches a point in the spout where the diameter of the particle exceeds that of the spout, particles of different diameters will initiate the breaking up of the spout at different heights in the spout. Thus, each particle, independent of its size, initiates its own break-up, and in the process, receives a coating appropriate to its size and shape. As a result, a coating can be applied to particles of different sizes and shapes, which, as shown in FIG. 2c, conforms to the specific size and shape of the particle.

In addition to coating particles of different sizes and shapes, the inventive technique is also particularly useful for coating individual small particles that have a tendency to coalesce into a larger conglomeration of particles. When particles to be coated are coalesced in the lower fluid, the surface tension forces and the increasing velocity of the flow as the particles are drawn upwardly in the spout act to pull the individual particles apart. This effect may be observed in FIG. 2b, wherein previously-coalesced poppy seeds have been pulled apart in the spout, and are shown rising individually. As shown in the figure, as the particles are pulled apart, the spout begins to break apart between each pair of them, so that the final result is three separately-coated particles. Thus, the inventive method is particularly advantageous for coating particles that are prone to coalesce, such as cells, since each particle may be individually coated. Alternatively, it is also possible to apply a single coat to a large conglomeration of cells. This may be accomplished by methods such as utilizing specific particles which have attractive forces between them that exceed the strength of the forces acting to pull them apart as they are drawn up the spout, or by establishing the parameters of the operation such that the particles are coated prior to the time when they would otherwise be pulled apart in the spout.

The rate at which particles may be coated by the inventive method is dependent on several factors. One significant factor is the density of the particles in the lower fluid near the interface of the two fluids and in the vicinity of the tube orifice. Preliminary testing indicates that the coating rate is quite high when particles are densely arranged in this area. With a single tube and appropriate suction, it is estimated that several hundred particles can be coated per second. When very large numbers of particles are to be coated, the system can be altered to include more than one withdrawal tube. Thus, for example, if a fluid contains $5 \times 10^5$ particles to be coated, the system could be altered to include additional withdrawal tubes. Theoretically, a system with ten tubes could perform such an operation in about 5 minutes. Thus, the number of tubes utilized in the system is dictated primarily by the number of particles to be coated. The additional tubes could be arranged to draw suction from the same suction pump as before, or from one or more additional pumps if additional suction capacity is required. If additional tubes and/or pumps are utilized, such tubes and/or pumps need not necessarily have the same dimensions (or capacity) as existing tubes and/or pumps, such arrangement to be dictated primarily based upon the composition of the particular group of particles to be coated.

Although many of the variables discussed above must be considered when establishing a coating rate, those skilled in the art will be able to suitably adjust these factors for any particular application without undue experimentation.

Figures 3A, 3B:
FIG. 3*a* illustrates a polystyrene bead coated with the PEG polymer.
FIG. 3*b* shows a mid-plane illustration of the coated bead of FIG. 3*a*, wherein a fluorescent coating surrounds the coated bead.
Figure 4A:
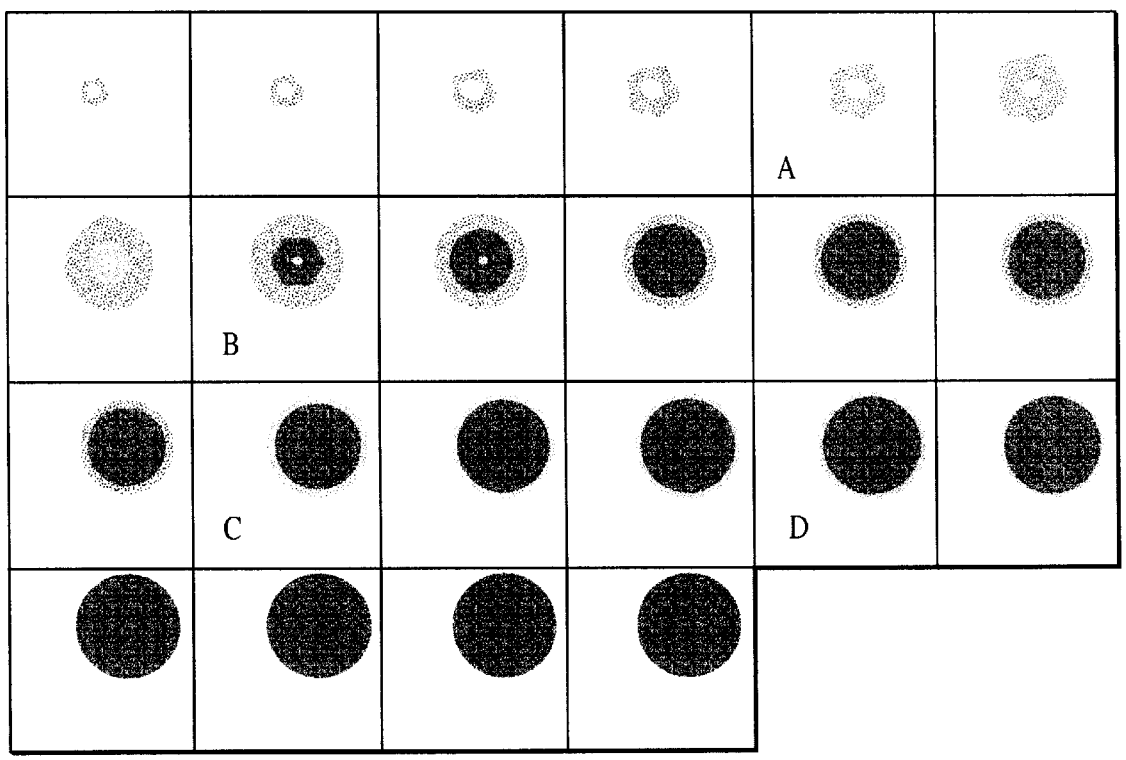
FIG. 4*a* is a series of confocal microscopy images of a polystyrene bead coated with a fluorescent agarose shell.

In a preferred embodiment of the invention, the lower (heavier) fluid comprises a pre-polymer fluid, which may then be polymerized and cross-linked to form a hard coating. Specific methods for cross-linking polymers are well-known in the art, and those skilled in the art will recognize that many such methods may be utilized to cross-link particles coated according to the present invention. For example, the polymer may be cross-linked utilizing optically active cross-linking methods. In this method, a light is shined on the tube above the point of break-off, so that the particle coating interacts with the light and cross-links. This is the method that was used to produce the coating on the bead shown in FIG. 3a. A second method is to arrange the tube in a temperature gradient. This can be accomplished, for example by positioning different portions of the tube in regions of different temperatures. Alternatively, the flow of encapsulated particles can be deposited in a second solution of lower temperature where they are hardened. The temperature gradient method was used to produce the confocal microscopy images in FIG. 4a. FIGS. 3a and 4a will be discussed in greater detail hereinafter. A third method is to use chemical initiation by flowing the coated particles into a regime where they contact a chemical that starts the cross-linking interaction. Encapsulating a particle in a cross-linked polymer according to these techniques provides that particle with a very hard and durable coating.

One example of optically-active cross-linking involves use of a coating of PEG, poly(ethylene glycol). PEG is well-known for its ability to prevent protein absorption, and, therefore, is a promising candidate for use as a base coating material for applications in which coated cells are to be transplanted into the body. When PEG is used as the lower fluid in the coating of cells, the cells are drawn up the tube, causing a break-up of the PEG spout as described above. At this point, the coating surrounding each of the cells is stabilized by cross-linking the PEG with ultraviolet light. If the tube is made of a material, such as quartz, that is transparent to UV radiation, cells with the polymeric coating can be illuminated with the light at any point during their transport above the point in which the spout breaks up. The duration of the radiation can be altered by methods such as extending the length of the tube, thereby flowing the particles over the light for a longer distance. This can be accomplished, for example, by making a long straight tube, or by making the tube into a coil, the entire length of which can be illuminated.

Other polymers, such as the bio-compatible polymers low-gelling agarose and poloxamer (poloxamers are non-ionic surfactants and include members of the group known as poly(oxyethylene)-poly(oxypropylene) block copolymers, available under the tradenames POLOXAMERS, PLURONIC and EMKALYX. Such copolymers are known commercially and are produced in a wide range of structures and molecular weights with varying contents of ethylene oxide. These non-ionic surfactants are non-toxic, stable and readily dispersible in aqueous systems), can be cross-linked by utilizing temperature gradients. In the case of agarose, cross-linking is initiated by lowering the temperature. With poloxamer, it is initiated by raising the temperature. In either case, the polymer is dissolved in the lower fluid containing the particles to be coated, such as cells, and the particles are drawn upwardly in the tube as described. A temperature gradient may be applied to the region of the tube in which the cells are flowing. For the agarose, the tube may be placed in or above a constant-temperature bath at an elevated temperature. For the polaxamer, it is placed in or above a bath at a depressed temperature. After the cross-linking has been accomplished, the temperature can be returned to its original level.

In addition to the foregoing procedures, interfacial chemistry can be used to advantage to carry out chemistry within droplets generated by selective withdrawal. In a prospective example of the use of this technique, selective withdrawal may be used to generate aqueous droplets that contain cells and a molecule (the pre-polymer) that contains an amino group and a carboxylic acid group. The addition of a carbodiimide reagent to this solution would activate the acids and lead to polymerization to generate a polyamide molecule. However, the use of diimide in this fashion is not practical because it is toxic to living cells. If the diimide is chosen so that it is soluble in the oil phase, but not the aqueous phase, then it will not pose a danger to the cells. Once the droplets are generated the diimide reagent can react with carboxylic acids at the interface between the two fluids, resulting in activation of the acid groups which subsequently react with the amino groups to generate polyamide. This strategy which takes advantage of the large increase in ratio of surface area to volume of the droplets permits toxic and water insoluble reagents to be used to effect chemistry in the droplets and represents an advantage of the present invention.

The specific examples provided above are illustrative of polymerization and cross-linking methods known in the art, and are not intended to be exclusive. Those skilled in the art will recognize that other known methods appropriate for a particular polymer may be substituted for those described above, when utilizing the teachings of the present invention.

Use of Coated Cells for Transplantation

Cells coated according to the inventive method may be used in cell transplantation applications, namely allo and xenotransplantation. Cell transplantation applications using encapsulated cells are disclosed in U.S. Pat. No. 5,871,767 (incorporated herein by reference in its entirety). Encapsulation provides immunoisolation of the cell by providing a semi-permeable barrier between the host and the transplanted tissue. The immunoisolation of transplanted cells by artificial barriers that permit crossover of low molecular weight substances, such as nutrients, electrolytes, oxygen, and bioactive secretory products, but prevent or substantially hinder crossover of immune cells and other transplant rejection compounds provides promise for tissue transplants in patients with various diseases, such as those diseases caused by the loss of specific vital metabolic functions.

A unique aspect of the encapsulated cells of the present invention is that cells of differing size may have the same coating thickness. Thus, a more uniform population of encapsulated cells can be produced. Furthermore, by being able to control the thickness of the coating irrespective of size of the cell, encapsulated cells derived from different origins may be made to have similar diffusive properties.

Cells coated according to the inventive method can provide for the implantation of diverse cell or tissue types. For example, the cells may be fully-differentiated, progenitor cells, or stem cells. They may be anchorage-dependent or anchorage-independent cells or tissue, fetal or neonatal, or transformed. The cells to be immunoisolated are prepared either from a donor (i.e., primary cells or tissues, including adult, neonatal, and fetal cells or tissues) or from cells which replicate in vitro (i.e., immortalized cells or cell lines, including genetically modified cells). In all cases, a sufficient quantity of cells to produce effective levels of the needed product or to supply an effective level of the needed metabolic function is prepared, generally under sterile conditions, and maintained appropriately (e.g. in a balanced salt solution such as Hank's salts, or in a nutrient medium, such as Ham's F12) prior to isolation.

The cells may require certain metabolic requirements from the host. Such metabolic requirements must diffuse through the coating of the encapsulated cells. The present invention provides for encapsulated cells with conformal coating, thus, greatly reducing the variation between particles in their ability to accept the metabolic requirements by diffusion through the coating.

Among the metabolic requirements met by diffusion of substances into the encapsulated cell is the requirement for oxygen. The oxygen requirements of the specific cells must be determined for the cell of choice. Methods and references for determination of oxygen metabolism are given in Wilson D. F. et al., J. Biol. Chem., 263, pp. 2712–2718, (1988). Also to be considered is the location in the body the encapsulated cells are to be placed.

In most cases, prior to implantation in vivo it will be important to use in vitro assays to establish the efficacy of the encapsulated cell for a particular purpose. This may be done using model systems. In a preferred embodiment of the instant invention, the diffusion of glucose into a sample of one or more encapsulated cells is used to stimulate insulin release from pancreatic islet cells. The appearance of insulin outside the encapsulated cells may be monitored through the use of an appropriately specific immunoassay. Such procedures allow the determination of the efficacy of the encapsulated cells on a per cell or unit volume basis.

Following the above guidelines, the actual number of cells to be implanted will then be determined by the amount of biological activity required for the particular application. In the case of secretory cells releasing therapeutic substances, standard dosage considerations and criteria known to the art will be used to determine the amount of secretory substance required. Factors to be considered include; the size and weight of the recipient; the productivity or functional level of the cells; and, where appropriate, the normal productivity or metabolic activity of the organ or tissue whose function is being replaced or augmented. It is also important to consider that a fraction of the cells may not survive the immunoisolation and implantation procedures, as well as whether the recipient has a preexisting condition which can interfere with the efficacy of the implant.

This invention also pertains to a method of isolating or protecting biologically active moieties, such as implanted cells, tissues, or other materials from immunological attack. The methods known in the art to produce encapsulated cells create a coating that is not conformal. Thus, whereas surfaces of the encapsulated cells of the prior art may be susceptible to immunodetection, the encapsulated cells of the present invention have conformal coatings to prevent the possibility of immunodetection.

The methods and compositions of the present invention are useful to deliver a wide range of cellular products, including high molecular weight products, to an individual in need of them, and/or to provide needed metabolic functions to an individual, such as the removal of harmful substances.

Products that can be delivered using the present invention include a wide variety of factors normally secreted by various organs or tissues. For example, insulin can be delivered to a diabetic patient, nerve growth factor (NGF) for patients with Alzheimer's disease, dopamine to a patient suffering from Parkinson's disease, growth hormone for treatment of dwarfism, or Factor VII & IX for a hemophiliac. Those skilled in the art will appreciate that the list provided above is not intended to be exclusive, but rather, is merely illustrative of uses to which the invention may be applied.

Other products that can be delivered through use of the compositions of the present invention include trophic factors such as Substance P, β-endorphin, and neurotensin. This invention is useful for treating individuals suffering from acute and/or chronic pain, by delivery of an analgesic or pain reducing substance to the individual. Such pain reducing substances include enkephalins, catecholamines and other opioid peptides. Such compounds may be secreted by, e.g., adrenal chromaffin cells.

Another family of products suited to delivery by the instant vehicle comprises biological response modifiers, including lymphokines and cytokines. Antibodies from antibody secreting cells may also be delivered. Specific antibodies that may be useful include those towards tumor specific antigens. The release of antibodies may also be useful in decreasing or deactivating circulating levels of compounds such as hormones, autoreactive or allergin reactive antibodies, or growth factors. These products are useful in the treatment of a wide variety of diseases, inflammatory conditions or disorders, and cancers.

The compositions of the present invention may also be used to restore or augment vital metabolic functions, such as the removal of toxins or harmful metabolites (e.g., cholesterol) from the bloodstream by cells such as hepatocytes. This method may be particularly useful for treating patients with liver failure, familial hypercholesterolemia, OTC deficiency, Criger-Najjar syndrome type 1, α1-antitrypsin deficiency, phenylketonuria, or other diseases.

The method and compositions of the instant invention make possible the implantation of cells without the concomitant need to immunosuppress the recipient for the duration of treatment, preferably providing homeostasis of particular substances by restoring and maintaining them for extended periods of time. Preferably, the number of encapsulated cells transferred is sufficient to provide an effective amount of the needed substance or function to an individual.

In one embodiment, the methods and compositions of the present invention may be used to treat patients with diabetes mellitus. Diabetes mellitus is the most common endocrine disease and is the fourth leading cause of death by disease in Western countries. Encapsulated pancreas islet cells (beta cells) may be used in such methods. Although the use of human insulin producing cells is within the scope of the present invention, insulin-producing pancreatic islets isolated from a wide variety of animal sources to produce animal insulins may be used. Animal insulins are fully active in humans and have been used in the treatment of diabetes for 70 years.

In an alternative embodiment, the source of the insulin producing cells is a beta cell line. A method of making a beta cell line is described by U.S. Pat. No. 5,902,577. This patent further discloses a preferred beta cell line, INS-I. The INS-I line is glucose-sensitive, has a high content of insulin, and has the possibility of expressing glucokinase and the glucose carrier Glut 2 at levels comparable with those of normal beta cells. Furthermore, the cells have been made non-proliferating by genetic engineering.

In preferred embodiments, before the transplant, it is desirable to make the cells non-proliferating. Indeed, the inhibition of proliferation is essential if it is desired to avoid uncontrolled growth and a possible destruction of the protective capsule. In the INS-I line or in similar cells, this is obtained by destroying the genes involved (directly or indirectly) in the cell proliferation. IGF-II is abundantly expressed in these cells. The inhibition of the expression of the IGF-II gene (by destroying the gene) is capable of inhibiting or of considerably reducing cell proliferation. By this genetic engineering, the INS-I cells are adapted to encapsulation and to transplantation by making it possible to avoid any complications and difficulties leading to the preparation and the transplantation of pancreatic islets.

U.S. Pat. No. 5,902,577 describes inactivation of the IGF-II gene by homologous recombination. However, the present inventors contemplate that essentially any method of gene inactivation including antisense technology may used to inactivate the IGF-II gene.

Furthermore, the proliferation of beta cells, which are genetically modified and cultured in the absence of serum, is considerably reduced when the cells are cultured in the presence of a binding protein IGFBP-3 (Gopinath R, Walton P. E., Etherton E. D.—Endocrinol 120:231–236 1989). The addition of IGFBP inhibits the proliferation of the INS-I cells.

Whether derived from primary isolates or cell lines, the encapsulated insulin-producing cells may be transplanted by a number of methods including subcutaneously or intraperitoneally. U.S. Pat. No. 5,902,577, demonstrates that the two methods are efficient in maintaining normoglycemia in the animal models of human insulin-dependent diabetes. The patent describes the use of biobreeding (BB) rats and the nonobese diabetic (NOD) mice which spontaneously develop diabetes (Lacy P, Hegre O. D., Gerasimidi-Vazeo A, Gentile F. T., Dionne K. E.—Science 254:1782–1784 1991) (Lanza R. P., Butler D. H., Borland K. M., Staruk J. E., Faustman D. L., Solomon B. A., Muller T. E., Rupp R. G., Maki T, Monaco A. P., Chick W. L.—Proc. Natl. Acad. Sci. 88:11100–11104 1991).

In another embodiment of this invention, methods are provided for the prevention or treatment of neural degeneration. Such neural degeneration occurs naturally as a result of the aging process, typically in physically mature individuals, or may occur as a result of a neurological disorder or disease. Examples of human diseases or disorders that are thought to be associated with neural degeneration include Alzheimer's disease, Amyotrophic Lateral Sclerosis, Huntington's chorea, AIDS-related dementia, and Parkinson's disease. These disorders often occur in physically mature individuals. However, these and other neurological disorders may occur in juveniles.

As used herein, an "aged" individual is an individual in whom neural degeneration has occurred or is occurring, either as a result of the natural aging process, or as a result of a neurodegenerative disorder. Neural degeneration as a result of the natural aging process means loss or decline of neural function compared to a previous state not attributable to a defined clinical abnormality or neurological disorder, such as Alzheimer's, Parkinson's or Huntington's.

Animal models for neurodegenerative conditions are based on the premise that a specific insult may damage or kill neurons. In some cases this may even lead to a cascade of neuronal death that affects trophically interdependent neurons along pathways responsible for specific brain functions.

A strategy for treatment of neural degenerative condition involves the localized administration of growth or trophic factors in order to (1) inhibit further damage to post-synaptic neurons, and (2) improve viability of cells subjected to the insult. Factors known to improve neuronal viability include basic fibroblast growth factor, ciliary neurotrophic factor, brain-derived neurotrophic factor, neurotrophin-3, neurotensin, and Substance P.

In one animal model for neurodegenerative excitotoxicity, the glutamate analog, quinolinic acid, is injected stereotaxically into the brain region known as the striatum and/or basal ganglia to produce neuropathology and symptoms analogous to those of patients suffering from Huntington's disease. Both the model and actual Huntington's disease are characterized by damage to neurons necessary for aspects of motor control.

Furthermore, one of the early symptoms of Huntington's disease is loss of body weight (Sanberg, P. R. et al. Med J Aust. 1, pp. 407–409 (1981). Similar effects are also seen in the model system (Sanberg, P. R. et al. Exp Neurol, 66, pp. 444–466 (1979). Quinolinic acid is also found at abnormally high levels in AIDS-related dementia.

In one embodiment of the present invention, trophic factors are provided to the proper brain region by implanting encapsulated cells that secret an appropriate factor. Suitably, the cells are adrenal chromaffin cells that are known to secrete at least one factor, basic fibroblast growth factor. Other as yet unidentified trophic factors may also be secreted by chromaffin cells. It is to be noted that this embodiment of the invention is separate from the use of chromaffin cells to secrete the neurotransmitter, dopamine, for the amelioration of symptoms of Parkinson's disease. Nerve growth factor-secreting cells such as fibroblasts engineered to express NGF represent an alternative therapy for this quinolinic acid induced neurodegeneration. Schwann cells prepared from myelin may be encapsulated and implanted in appropriate brain areas to prevent neural degeneration associated with Parkinson's disease.

In another embodiment of the invention, the animal model involves lesion of the fimbria-fornix. In particular, neurons of the septohippocampal system are axotomized leading to degeneration and cell death. This model is thought to be analogous to the types of lesions that cause Alzheimer's disease in humans. Suitably, a growth factor, nerve growth factor (NGF), is provided by the implantation of encapsulated cells that secrete NGF. Astrocytes immortalized (e.g. by transforrnation with the Large T antigen) and genetically engineered to express NGF may be employed. Preferably, the cells are fibroblasts that have been genetically engineered to produce recombinant NGF. The fibroblasts survive best in a core composed of a matrix material that mimics extracellular matrix, such as collagen or laminin-containing hydrogels. The core is surrounded by an immunoisolatory jacket that allows the diffusion of oxygen and nutrients to the cells in the core, and also allows the secreted NGF to diffuse through the jacket and into the body of the recipient. The implant inhibits the death of cholinergic neurons as assayed by the number of neurons that contain choline acetyl transferase (ChAT), an indicator of viable cholinergic neurons.

Fimbria-fornix lesions also cause behavioral deficits in the animal subjects of the model, most easily observed in tasks involving learning and memory. It has been reported that chronic administration of NGF to rats with fimbria-fornix lesions accelerates the animals' behavioral recovery (Wills, B. et al. Behav. Brain Res., 17, pp. 17–24 (1985)). In an embodiment of the present invention, implantation of encapsulated NGF-secreting cells provides a practical way to deliver NGF continuously to the appropriate brain region of the lesioned animal. By analogy, the encapsulated cells of the present invention offer a practical form of regenerative and/or prophylactic therapy for Alzheimer's victims whose conditions may be ameliorated by continuous delivery of NGF to specific brain regions.

A wide variety of biologically active moieties or cells may be used in this invention. These include well known, publicly available immortalized cell lines as well as primary cell cultures. Examples of publicly available cell lines suitable for the practice of this invention include, baby hamster kidney (BHK), chinese hamster ovary (CHO), mouse fibroblast (L-M), NIH Swiss mouse embryo (NIH/3T3), African green monkey cell lines (including COS-a, COS-7, BSC-1, BSC-40, BMT-10 and Vero), rat adrenal pheochromocytoma (PC12) and rat glial tumor (C6). Primary cells that may be used according to the present invention include, adrenal cell fetal nerve cells, parathyroid cells, bFGF-responsive neural progenitor-stem cells derived from the CNS of mammals (Richards et al., Proc. Natl. Acad. Sci. USA 89, pp. 8591–8595 (1992); Ray et al., Proc. Natl. Acad. Sci. USA, 90, pp. 3602–3606 (1993)), primary fibroblasts, Schwann cells, astrocytes, .beta.-TC cells, Hep-G2 cells, AT T20 cells, oligodendrocytes and their precursors, myoblasts, adrenal chromaffin cells, and the like.

Schwann cells maybe prepared according to the method of Bunge (PCT published application WO 92/03536), mixed with a suitable substratum such as Matrigel.TM, and encapsulated. The encapsulated cells may be implanted in appropriate areas of the brain to prevent the degeneration of the dopaminergic neurons of the nigral striatal pathway associated with Parkinson's disease. Generally, the preferred implant site will be in or near the striatum. Encapsulating the cells may enhance secretion of trophic factors since the cells will not be in proximal contact with neurons, and myelination will not occur. Other glial cell types may be encapsulated and implanted for this purpose, including astrocytes and oligodendrocytes.

The choice of biologically active moiety or cell depends upon the intended application. The encapsulated cells may be chosen for secretion of a neurotransmitter. Such neurotransmitters include dopamine, gamma aminobutyric acid (GABA), serotonin acetylcholine, noradrenaline, epinephrine, glutamic acid, and other peptide neurotransmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor.

The encapsulated cells can also be chosen for their secretion of hormones, cytokines, growth factors, trophic factors, angiogensis factors, antibodies, blood coagulation factors, lymphokines, enzymes, and other therapeutic agents or agonists, precursors, active analogs, or active fragments thereof. These include enkephalins, catecholamines, endorphins, dynorphin, insulin, factor VIII, erythropoietin, Substance P, nerve growth factor (NGF), Glial derived Neurotrophic Factor (GNDF), platelet-derived growth factor (PDGF), epidermal growth factor (EGF), brain-derived neurotrophic factor (BDNF), neurotrophin-3 (NT-3), an array of fibroblast growth factors, and ciliary neurotrophic factor.

Alternatively, one or more biologically active molecules may be delivered into the encapsulated particle or cell. For example, the encapsulated particle or cell may "scavenge" cholesterol, or other biological factors, from the host.

Techniques and procedures for isolating cells or tissues that produce a selected product are known to those skilled in the art, or can be adapted from known procedures with no more than routine experimentation. For example, islets of Langerhans can be isolated from a large-animal pancreas (e.g., human or porcine) using a combination of mechanical distention and collagenase digestion, as described by Scharp, D. W., et al., U.S. Pat. No. 4,868,121. Islets may be isolated from small animals such as rats by the method of Scharp, et al., Diabetes 29, suppl. 1, pp. 19–30 (1980). Similarly, hepatocytes can be isolated from liver tissue using collagenase digestion followed by tissue fractionation, as described by Sun, A. M., et al., Biomat., Art. Cells, Art. Org., 15, pp. 483–496 (1987). Adrenal chromaffin cells may be isolated by the method of Livett, B. G., Physiology Reviews, 64, pp. 1103–1161 (1984).

Many cellular products that are difficult to provide using primary donor tissues can be provided using immortalized cells or cell lines. Immortalized cells are those which are capable of indefinite replication but which exhibit contact inhibition upon confluence and are not tumorigenic. An example of an immortalized cell line is the rat pheochromocytoma cell line PC 12. Transformed cells or cell lines can be used in a similar manner. Transformed cells are unlike merely immortalized cells in that they do not exhibit contact inhibition upon confluence, and form tumors when implanted into an allogeneic host. Immortalization can allow the use of rare or notoriously fragile cell or tissue types for the long-term delivery of a chosen product or metabolic function. Suitable techniques for the immortalization of cells are described in Land H. et al., Nature 304, pp. 596–602 (1983) and Cepko, C. L., Neuron 1, pp. 345–353 (1988). Candidate cell lines include genetically engineered beta-cell lines which secrete insulin such as NIT cells (Hamaguchi, K., et al., Diabetes 40, p. 842 (1991)), RIN cells (Chick, W. L., et al., Proc. Natl. Acad. Sci. USA, 74, pp. 628–632 (1977)), ATT cells (Hughes, S. D., et al, Proc. Natl. Acad. Sci. USA, 89, pp. 688–692 (1992)), CHO cells (Matsumoto, M., et al, 1990, Proc. Natl. Acad. Sci. USA, 87, pp. 9133–9137 (1990)), and beta-TC-3 cells (Tal, M., et al, 1992, Mol. Cell Biol., 12, pp. 422–432 (1992)). Additionally, recombinant cells or cell lines can be engineered to provide novel products or functions and combinations thereof, using a wide variety of techniques well known to those of ordinary skill in the art.

For example, fibroblasts can be transfected with an expression vector for the chosen product (e.g., nerve growth factor, erythropoietin, insulin, or Factor VIII). It should be recognized however, that expression of a recombinant protein in a cell type which does not normally express the protein may lead to unregulated expression which may not be desirable for certain medical applications.

B-cell hybridomas secreting a selected monoclonal antibody, or T-cell hybridomas secreting a selected lymphokine, can also be used. It may be particularly desirable to deliver a monoclonal antibody or fraction thereof, which neutralizes the biological activity of a disregulated biological response modifier using the instant invention. Engineered cells that secrete soluble fragments of receptors for these biological response modifiers can be used in a similar fashion. The disregulation or overproduction of particular biological response modifiers has been implicated in the etiology of certain cancers.

The encapsulated cells may secrete such antinociceptive agents, including any one of catecholamines, enkephalins, opioid peptides or mixtures thereof. Preferably catecholamines are secreted, most preferably a mixture of catecholamines and enkephalins. Typically, the encapsulated cells are derived from the adrenal medulla, or more particularly, are adrenal medulla chromaffin cells. Additionally, genetically engineered cell lines or other naturally occurring cell lines able to secrete at least one pain reducing agent such as a catecholamine, enkephalin, opioid peptide, or agonist analog thereof, can be used.

If the cells to be immunoisolated are replicating cells or cell lines adapted to growth in vitro, it is particularly advantageous to generate a cell bank of these cells. A particular advantage of a cell bank is that it is a source of cells prepared from the same culture or batch of cells. That is, all cells originated from the same source of cells and have been exposed to the same conditions and stresses. Therefore, the vials can be treated as identical clones. In the transplantation context, this greatly facilitates the production of identical or replacement immunoisolatory vehicles. It also allows simplified testing protocols that assure that implanted cells are free of retroviruses and the like. It may also allow for parallel monitoring of the encapsulated cells in vivo and in vitro, thus allowing investigation of effects or factors unique to residence in vivo.

In all cases, it is important that the cells contained in the vehicle are not contaminated or adulterated. If an encapsulated particle comprising a matrix core is desired, the encapsulated cells are produced under sterile conditions, with an appropriate amount of a biocompatible, gellable hydrogel matrix precursor. There are numerous natural and synthetic hydrogels that may be suitable for use in the methods and compositions of the present invention. Suitable naturally-derived hydrogels include plant-derived gums, such as the alkali metal alginates and agarose, and other plant-derived substances, such as cellulose and its derivatives (e.g., methylcellulose). Animal tissue-derived hydrogels such as gelatin are also useful. Alternatively, the matrix can be made of extracellular matrix (ECM) components, as described by Kleinman et al., U.S. Pat. No. 4,829,000. Suitable synthetic hydrogels include polyvinyl alcohol, block copolymer of ethylene-vinylalcohol, sodium polystyrene sulfonate, vinyl-methyl-tribenzyl ammonium chloride and polyphosphazene (Cohen, S. et al. J. Anal. Chem. Soc., 112, pp. 7832–7833 (1990)).

The encapsulated particles obtained by any of the methods described herein can be maintained under sterile conditions in a non-pyrogenic, serum-free defined nutrient medium or balanced salt solution, at about 37° C., prior to implantation. Lower temperatures (20° C.–37° C.) may be optimal for certain cell types and/or culturing conditions. Other holding temperatures and medium compositions consistent with good cell viability may also be used. Alternatively, the vehicle can be cryopreserved in liquid nitrogen, if a cryoprotective agent such as glycerin has been incorporated (Rajotte, R. V. et al. Transplantation Proceedings, 21, pp. 2638–2640 (1989)). In such a case, the vehicle is thawed before use and equilibrated under sterile conditions as described above.

Preferably, implantation of the encapsulated particles is also performed under sterile conditions. In some embodiments, the encapsulated particles are implanted at a site in the recipient's body that will allow appropriate delivery of the secreted product or function to the recipient and of nutrients to the implanted cells or tissue, while also allowing access to the encapsulated particles for retrieval and/or replacement. It is considered preferable to verify that the cells function properly both before and after implantation; assays or diagnostic tests well known in the art may be used for these purposes. For example, an ELISA (enzyme-linked immunosorbent assay), chromatographic or enzymatic assay, or bioassay specific for the secreted product can be used. If desired, secretory function of an implant can be monitored over time by collecting appropriate samples (e.g., serum) from the recipient and assaying them.

Encapsulating Particles with Reflective and/or Anti-reflective Coatings

Using the inventive method, particles can be coated with materials having different indices of refraction. If the coatings are made thin enough, they will be on the order of the wavelength of light, and thus, can be made to selectively be reflective or anti-reflective in different wavelength regimes. Thus, coatings could be made that block out or transmit infrared, visible or ultraviolet light.

Encapsulating Particles with a Plurality of Layers

Using the inventive method, three, four or even more thin layers of fluids may be added to the container. If an intermediate fluid that forms a spout comprises a thin layer, the spout will also entrain some of the fluid in the layer(s) below it (or above it if it is being sucked in the downward direction). Thus, the rising (or falling) fluid may comprise respective segments made up of three or more fluids. If three layers are present, the coatings will comprise a thick outer coating layer, a thin intermediate layer, and an inner core from the bottom-most fluid. This could prove to be a rapid method of applying multiple coatings on a particle, or alternatively, to form particles made up of the several different layers.

As another alternative, a density gradient may be incorporated into the entrained fluid. In this case, different salinity concentrations would be established for different depths in the entrained fluid. When the selective withdrawal process is initiated, a sphere of water is formed having a salinity gradient inside. In this instance, the core would have a greater concentration of salt than the outer part of the sphere. In the event one uses a different chemical as a gradient this procedure would translate. This application may be useful in a drug delivery process, where the dose needs to increase with time. This alternative procedure may be used in conjunction with the process for coating several layers as described above to produce any number of complicated layering.

Another variant of this technique that may be used to coat particles with a plurality of layers involves the initial coating of a particle utilizing the method described in Examples 1–3, above, and then returning the particles with the hardened coating to the lower fluid, or alternatively, placing them in another container having the same or a different combination of fluids. The coated particles can then be run through the process as many times as desired to obtain the desired layers of coating.

Sorting Cells According To Their Properties

The inventive selective withdrawal method may also be used to sort particles according to differences in their chemical or physical properties. For example, particles may be sorted according to differences in density or magnetic strength. Since the only particles entrained in the exit flow are normally those found at the interface between the two fluids, more dense particles will lie below the surface and not be entrained in the flow. Likewise, if some particles are attached to a magnetic particle, such as a ferrofluid, a small magnet may be placed just below the spout to pull those particles out of the surface and keep them from being entrained in the flow. This process can be useful for sorting islet cells from others.

Combined Cell Transplant

The invention may be used for combined cell transplant and local delivery of other compositions. Such compositions include growth factors, local immunosuppressive drugs, or anti-inflammatory drugs.

Coating of Microcarrier Beads

Microcarrier beads may be coated with polymers for cell culturing. For example, magnetic beads may be coated by the method of the present invention, wherein the coating contains a molecule such as an antibody or ligand that attaches to a particular cell type. Such beads will have particular utility in methods of isolating those particular cells away from other cells or removing the cells from a solution.

Targeting

In one embodiment, the coating contains proteins or other molecules that facilitate attachment of the coated particle to a particular cell or organ type. Such coated particles may be produced by a number of ways including, by polymerization of the coating in the presence of the protein or other molecule or by modifying the coated particle after encapsulation. By being able to attach to specific cells or tissues, the coated particles may be used to target therapeutic or toxic agents to those particular cells (e.g., cancer therapy).

Imaging

The method of the present invention can be used in other diverse applications, including production of particles for photographic imaging (see for example, Silence et al, U.S. Pat. No. 5,900,344).

A wide range of materials can be used as imaging agents, including ionic materials; relatively low molecular weight non-ionic materials; site-specific materials; particulate materials; and relatively high molecular weight non-ionic or substantially non-ionic materials. (It is of course possible for one material to belong to more than one of these categories).

Insofar as ionic materials are concerned, particular mention should be made of the ionic materials already proposed in the literature for use as Electrical impedance imaging (EII), X-ray and Magnetic Resonance Imaging (MRI) agents. Examples of such materials include many compounds with extremely low toxicity even compared with saline, and compounds may be selected which distribute preferentially within the body, e.g. that congregate at particular tissues, organs or tissue abnormalities or that are essentially confined to the circulatory system and act as blood pool agents. Examples of ionic X-ray contrast agents suited for use according to the present invention include in particular the iodinated contrast agents, especially those containing one or more, generally one or two, triiodophenyl groups in their structure. The counterion for any such imaging agent should itself be physiologically tolerable and can be, for example, alkali and alkaline earth metal cations and cations deriving from organic bases, especially sodium, zinc and ammonium ions, and more especially lysine, calcium and meglumine.

Particular ionic X-ray contrast agents useful according to the invention thus include physiologically acceptable salts of 3-acetylamino-2,4,6-triiodobenzoic acid, 3,5-diacetamido-2,4,6-triiodobenzoic acid, 2,4,6-triiodo-3,5-dipropionamido-benzoic acid, 3-acetylamino-5-((acetylamino)methyl)-2,4,6-triiodobenzoic acid, 3-acetylamino-5-(acetylmethylamino)-2,4,6-triiodobenzoic acid, 5-acetamido-2,4,6-triiodo-N-((methylcarbamoyl)methyl)-isophthalamic acid, 5-(2-methoxyacetamido)-2,4,6-triiodo-N->2-hydroxy-1-(methylcarbamoyl)-ethy 1-isophthalamic acid, 5-acetamido-2,4,6-triiodo-N-methylisophthalamic acid, 5-acetamido-2,4,6-triiodo-N-(2-hydroxyethyl)-isophthalamic acid, 2->>2,4,6-triiodo-3>(1-oxobutyl)-aminophenylmethyl!butanoic acid, beta-(3-amino-2,4,6-triiodophenyl)-alpha-ethyl-propanoic acid, 3-ethyl-3-hydroxy-2,4,6-triiodophenylpropanoic acid, 3->>(dimethylamino)-methyl!amino!-2,4,6-triiodophenyl-propanoic acid (see Chem. Ber. 93:2347 (1960)), alpha-ethyl-(2,4,6-triiodo-3-(2-oxo-1-pyrrolidinyl)-phenyl)-propanoic acid, 2->2->3-(acetylamino)-2,4,6-triiodophenoxy!ethoxymethyl!butanoic acid, N-(3-amino-2,4,6-triiodobenzoyl)-N-phenyl-.beta.-aminopropanoic acid, 3-acetyl-(3-amino-2,4,6triiodophenyl)amino!-2-methylpropanoic acid, 5->(3-amino-2,4,6-triiodophenyl)methylamino!-5-oxypentanoic acid, 4->ethyl->2,4,6-triiodo-3-(methylamino)phenyl!amino!-4-oxo-butanoic acid, 3,3'-oxybis>2,1-ethanediyloxy-(1-oxo-2,1-ethanediyl)imino!bis-2,4,6-triiod obenzoic acid, 4,7,10,13-tetraoxahexadecane-1,16-dioyl-bis(3-carboxy-2,4,6-triiodoanilide), 5,5"-(azelaoyidiimino)-bis>2,4,6-triiodo-3-(acetylamino)methyl-benzoic acid, 5,5'-(apidoldiimino)bis(2,4,6-triiodo-N-methyl-isophthalamic acid), 5,5'-(sebacoyl-diimino)-bis(2,4,6-triiodo-N-methylisophthalamic acid), 5,5->N,N-diacetyl-(4,9-dioxy-2,11-dihydroxy-1,12-dodecanediyl)diimino!bis(2,4,6-triiodo-N-methylisophthalamic acid), 5,5'5"-(nitrilo-triacetyltriimino)tris (2,4,6-triiodo-N-methyl-isophthalamic acid), 4-hydroxy-3,5-diiodo-alpha-phenylbenzenepropanoic acid, 3,5-diiodo-4-oxo-1(4H)-pyridine acetic acid, 1,4-dihydro-3,5-diiodo-1-methyl-4-oxo-2,6-pyridinedicarboxylic acid, 5-iodo-2-oxo-1(2H)-pyridine acetic acid, and N-(2-hydroxyethyl)-2,4,6-triiodo-5->2->2, 4,6-triiodo-3-(N-methylacetamido)-5-(methylcarbomoyl) benzamino!acetamido!-isophthalamic acid, as well as other ionic X-ray contrast agents proposed in the literature e.g. in J. Am. Pharm. Assoc., Sci Ed. 42:721 (1953), CH-A-480071, JACS 78:3210 (1956), DE-A-2229360, U.S. Pat. No. 3,476,802, Arch. Pharm. (Weinheim, Ger) 306:11 834 (1973), J. Med. Chem. 6:24 (1963), FR-M-6777, Pharmazie 16:389 (1961), U.S. Pat. Nos. 2,705,726, 2,895,988, Chem. Ber. 93:2347 (1960), SA-A-68/01614, Acta Radiol. 12:882 (1972), GB-A-870321, Rec. Trav. Chim. 87:308 (1968), East German Patent 67209, DE-A-2050217, DE-A-2405652, Farm Ed. Sci. 28:912 (1973), Farm Ed. Sci. 28:996 (1973), J. Med. Chem. 9:964 (1966), Arzheim.-Forsch 14:451 (1964), SE-A-344166, U.S. Pat. No. 1,993,039, Ann 494:284 (1932), J. Pharm. Soc. (Japan) 50:727 (1930), and U.S. Pat. No. 4,005,188. The disclosures of these are incorporated herein by reference.

Besides ionic X-ray contrast agents, such as those mentioned above, one may advantageously use as imaging agents the ionic compounds (such as for example GdDTPA and GdDOTA) which have been proposed for use as MRI contrast agents, especially the salts of paramagnetic metal complexes (preferably chelate complexes) with physiologically compatible counterions, as well as similar complexes in which the complexed metal ion is diamagnetic (as paramagnetism is not a property required for the imaging agent to function as such). Preferred complexed paramagnetic metal ions will include ions of Gd, Dy, Eu, Ho, Fe, Cr and Mn and preferred non paramagnetic complexed ions will include ions of Zn, Bi and Ca.

The complexing agent will preferably be a chelating agent such as a linear, branched or cyclic polyamine or a derivative thereof, e.g. a polyaminocarboxylic acid or a polyaminopolyphosphonic acid or a derivative of such an acid, e.g. an amide or ester thereof. Particular mention in this regard may be made of DTPA, DTPA-bisamides (e.g. DTPA-bismethylamide and DTPA-bismorpholide), DTPA-bis (hydroxylated-amides), DOTA, DO3A, hydroxypropyl-DO3A, TETA, OTTA (1,4,7-triaza-10-oxa-cyclododecanetricarboxylic acid), EHPG, HIDA, PLED, DCTA and DCTP as well as the other chelating agents mentioned in the literature, e.g. in U.S. Pat. No. 4,647,447, WO-A-86/02841, EP-A-130934, U.S. Pat. Nos. 4,826,673, 4,639,365, EP-A-71564, EP-A-165728, EP-A-232751, EP-A-230893, EP-A-292689, EP-A-287465, DE-A-3633245, DE-A-3324235, EP-A-250358, EP-A-263059, EP-A-173163, EP-A-255471, U.S. Pat. No. 4,687,659, WO-A-86/02005, WO-A-87/02893, WO-A-85/05554, WO-A-87/01594, WO-A-87/06229, WO-A-90/08138 and WO-A-90/08134.

Several such chelates are inherently site-specific (e.g. the hepatobiliary contrast agents of EP-A-165728). Otherwise chelating moieties may be attached to macromolecular carriers to yield site-specific contrast agents the site specificity of which derives primarily from the nature of the macromolecule. Thus, for example, by coupling chelating moieties to physiologically relatively inert high molecular weight (e.g. greater than 40 KD) dextrans, a blood pool agent may be produced (see EP-A-186947). Alternatively chelating moieties may be coupled directly or indirectly, e.g. via a polymer linker such as polylysine or polyethyleneimine, to biologically active molecules, such as monoclonal antibodies etc., thereby producing a tissue- or organ-targeting contrast agent.

Particulate contrast agents, if administered into the cardiovascular system, will tend to be abstracted by the reticuloendothelial system and thus are particularly suited for use in imaging the liver.

One form of particulate imaging agent which may be used according to the invention comprises magnetically locatable particles, especially ferromagnetic, ferrimagnetic and in particular superparamagnetic particles. Such particles have been proposed for use as MRI contrast agents and generally are metallic or are of magnetic metal oxides, e.g. ferrites.

Particular mention in this regard may be made of the superparamagnetic contrast agents proposed for use as MRI contrast agents by Jacobsen et al. in U.S. Pat. No. 4,863,716, by Klaveness et al. in WO-A-89/11873, by Schroder et al. in WO-A-85/02772, by Groman in WO-A-88/00060, by Schering in EP-A-186616, by Widder et al. in AJR 148:399–404 (1987), by Hemmingsson et al. in Acta Radiologica 28:703–705 (1987), by Hahn et al. in Society of Magnetic Resonance in Medicine, 7th Annual Meeting, 1988, Book of Abstracts, page 738, by Saini et al. in Radiology 162:211–216 (1987), and by Clement et al. in CMR89. MR20 (1989).

Superparamagnetic particles, both free and carrier-bound, are widely available and their preparation is described in a large variety of references, e.g. WO-A-83/03920 (Ugelstad), WO-A-89/03675 (Schroder), WO-A-83/03426 (Schroder), WO-A-88/06632 (Josephson), U.S. Pat. No. 4,675,173, DE-A-3508000 and WO-A-88/00060.

Superparamagnetic particles can be administered either free (i.e. uncoated and not bound to any other substance) or coated (e.g. dextran coated—see for example U.S. Pat. No. 4,452,773) or carried by or embedded in a matrix particle (e.g. a polysaccharide—see for example WO-A-83/03920 and WO-A-85/02772) or bound to an organ- or tissue-targeting species, e.g. a biomolecule such as an antibody or a hormone (see for example WO-A-88/00060 and WO-A-88/06632).

Particular mention may also be made of the use of metallic, that is, conducting particles. These may be used as dispersions of free particles but more generally the particles will be coated by or embedded in or on a physiologically tolerable matrix material such as those discussed above. Similarly solutions or dispersions of conducting polymers may also advantageously be used as Imaging media.

Further examples of particulate contrast media useful as Imaging media, especially as negative contrast media include the entrapped gas containing particles previously suggested as contrast agents for ultrasound, e.g. Albumex available from Molecular Biosystems Inc, California. Other microbubble or microballoon containing or generating materials, e.g. microvesicles, may also be used.

Particulate contrast agents for parenteral administration should preferably have particle sizes of no more than 1.5 $\mu$m, especially 1.0 $\mu$m or less.

Other examples of contrast agents that may be used include zeolites and fullerenes, optionally in ionic form and optionally acting as carriers for metal ions. Besides the closed-cage fullerenes, other carbon mesh framework materials such as graphite and the so called "bucky-tubes" may be used as well as their derivatives (e.g. intercalates). Many such materials are known from the literature. Particular reference is made to the disclosures of PCT/EP92/02550 and GB 9203037.8 which are incorporated herein by reference.

Special mention should also be made of biodegradable contrast agents, especially those containing ester or carbonate groups, which break down in vivo to produce ionic groups or to liberate smaller molecular ions, for example by releasing a chelant molecular ion from a macromolecular carrier (which may itself be soluble or particulate). Examples of such biodegradable contrast agents also include certain non-ionic X-ray contrast agents which are pro-drugs for ionic X-ray contrast agents, e.g. ethyl 10-(4-iodophenyl) undecylate and 3,5-diiodo-4-oxo-1(4H) pyridineacetic acid propyl ester. Reference in this regard is also made to the disclosures of JACS 64:1436 (1942), WO-A-89/00988 and WO-A-90/07491.

Non-ionic materials, and ionic compounds with very low charge to mass ratios can be used, if desired, as negative contrast agents especially where high concentrations can be used—as for example in the case with the non-aqueous blood substitutes. However it is also thought possible that at very high frequencies in the impedance measurement even non-ionic compounds may serve to modify the impedance of an aqueous solution. Accordingly the invention does extend to cover the use of non-ionic X-ray contrast agents and non-ionic paramagnetic or diamagnetic metal chelate complexes.

Examples of suitable non-ionic X-ray contrast agents include metrizamide, iopamidol, iohexol, iotrolan, iodecimol, iodixanol, ioglucol, ioglucomide, ioglunide, iogulamide, iomeprol, iopentol, iopromide, iosarcol, iosimide, iotasul, ioversol and ioxilan (see for example DE-A-2031724, BE-A-836355, GB-A-1548594, EP-A-33426, EP-A-49745, EP-A-108638, U.S. Pat. No. 4314055, BE-A-846657, DE-A-2456685, BE-A-882309, EP-A-26281, EP-A-105752, DE-A-2909439, DE-A-3407473, DE-A-3001292, EP-A-22056, EP-A-83964 and WO-A-87/00757). Examples of suitable non-ionic MRI contrast agents include Gd-DTPA.BMA, Gd-HP-DO3A, and Dy DTPA.BMA.

Parenteral administration of contrast agents according to the invention will generally be by injection or infusion, especially into the cardiovascular system. However the contrast media may also be administered into body cavities having external voidance ducts, e.g. by catheter into the bladder, uterus etc. Moreover, the iodinated contrast agents, the magnetically targetable or electrically conductive contrast agents and the non-radioactive metal chelate contrast agents discussed above may also be used advantageously in imaging of the gastrointestinal tract and such use and the use of such materials for the manufacture of imaging media for enteral administration constitute further aspects of the present invention.

The dosages of imaging media used according to the invention will vary over a broad range depending on a variety of factors such as administration route, the pharmacodynamic properties of the contrast agent (the more widely distributing the agent is the larger the dose may be), the chemical and physical nature of the contrast agent, and the frequency of the electrical current applied in the impedance measurement.

Typically however agents will be administered in concentrations of 1$\mu$mol/l to 1mol/l, preferably $10^{-2}$ to 10 mmol/l and dosages will lie in the range 0.002 to 20 mmol/kg bodyweight, generally 0.05 to 5 mmol/kg. For matrix bound, carried or encapsulated contrast agents the overall dosage will generally be 1 to 100 ml when administered into the cardiovascular system or 10 ml to 1.5 liters of contrast media when administered into a body cavity having an external voidance duct, e.g. by oral or rectal administration.

Imaging in accordance with the particles of the present invention may be performed for a wide range of clinical indications with appropriate selection of the imaging agent (for its pharmacodynamic properties) and of the administration route. Thus non-absorbable imaging agents are particularly useful for imaging of the gastrointestinal tract for diagnosis of abnormalities therein or as markers of the gastrointestinal system. Such agents may also be used for dynamic studies, for example of gastric emptying. In studies of the gastrointestinal tract, it may be advisable to use an agent such as cimetidine to suppress naturally occurring pH variations which might otherwise reduce imaging accuracy.

The clinical indications for parenteral imaging agents include CNS examination, perfusion studies, blood pool imaging, examination of body cavities, of the pelvic region and of the kidneys, hepatobiliary studies and studies of liver and kidney function, tumor imaging, and diagnosis of infarcts, especially in the heart.

Other Applications

Other prospective applications of the selective withdrawal technology do not require particle encapsulation. Among these are the following:

Drug Delivery

The method of the present invention can be used to encapsulate a therapeutically effective amount of an agent for topical or subcutaneous application to a selected tissue of a patient, wherein said therapeutic agent is selected from the group consisting of anti-fungal agents, hormones, vitamins, peptides, enzymes, anti-allergic agents, anti-coagulation agents, antituberculars, antivirals, antibiotics, antibacterials, antiinflammatory agents, antiprotozoans, local anesthetics, growth factors, cardiovascular agents, diuretics, and radioactive compounds.

Suitable anti-fungal agents include ketoconazole, nystatin, griseofulvin, flucytosine, miconazole, amphotericin B and the like.

Suitable hormones include growth hormone, melanocyte stimulating hormone, estradiol, betamethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate and the like.

Suitable vitamins include Vitamin A, Vitamins B (1–12), Vitamin C, Vitamin D, Vitamin E (α-tocopherol), Vitamin K, β-carotene, cyanocobalamin neinoic acid, retinoids, retinol palmitate, ascorbic acid and the like.

Suitable amino acids, peptides and enzymes include the naturally occurring amino acids, manganese super oxide dismutase, alkaline phosphatase and the like.

A suitable anti-allergic agent incldue amelexanox and the like.

Suitable anti-coagulation agents include phenprocoumon, heparin and the like.

Suitable antituberculars include paraminosalicylic acid, isoniazid, capreomycin sulfate cycloserine, ethambutol hydrochloride ethionamnide, pyrazinamide, rifampin, streptomycin sulfate and the like.

Suitable antivirals include acyclovir, gancyclovir, amantadine azidothymidine, ribavirin, vidarabine monohydrate and the like.

Suitable antibiotics include dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin, tetracycline and the like.

Suitable antiinflammatories include diflunisal, ibuprofen, indomethacin, meclofenamate, mefenamic acid, naproxen, oxyphenbutazone, phenylbutazone, piroxicam, sulindac, tolmetin, aspirin, salicylates and the like.

Suitable antiprotozoans include chloroquine, hydroxychloroquine, metronidazole, quinine, meglumine antimonate and the like.

Suitable local anesthetics include bupivacaine hydrochloride, chloroprocaine hydrochloride, etidocaine hydrochloride, lidocaine hydrochloride, mepivacaine hydrochloride, procaine hydrochloride, tetracaine hydrochloride and the like.

Suitable growth factors include Epidermal Growth Factor, acidic Fibroblast Growth Factor, Basic Fibroblast Growth Factor, Insulin-Like Growth Factors, Nerve Growth Factor, Platelet-Derived Growth Factor, Stem Cell Factor, Transforming Growth Factor of the α-family, Transforming Growth Factor of the β-family and the like.

Suitable cardiovascular agents include clonidine, propranolol, lidocaine, nicardipine, nitroglycerin and the like.

Suitable diuretics include mannitol, urea and the like.

Suitable radioactive agents include strontium, iodine, rhenium, yttrium and the like.

The lower fluid level may be arranged to contain a mixture of pre-polymer and a pharmaceutical compound such that polymerization of this mixture confined in a droplet provides a polymer that contains an entrapped or cross-linked pharmaceutical reagent. With an appropriate choice of polymer, such materials can be utilized as transplantable materials for localized or systemic drug release. This method has the distinction that it permits the fabrication of materials that release different pharmaceuticals and drugs at different time intervals. In this prospective example, a polymer bead loaded with one drug can subsequently be coated with the same or a different polymer bearing a second drug. This process can be repeated any number of times to afford spherical particles that control the composition of drugs in each shell of the coating. Such a method provides control in tailoring the release of drugs and pharmaceuticals, such as at an implant site. Additionally, a multi-layer structure including a drug in each layer can be prepared utilizing selective withdrawal through multiple layers of fluid.

Preparation of Mono-Dispersed Spherical Articles

When the lower fluid is drawn into the tube via selective withdrawal, the spout eventually becomes unstable and breaks up into little droplets. These droplets can be polymerized (using light or Temperature etc.) to form hard mono-dispersed spheres. When a spout breaks up, tiny satellite drops are produced in addition to the main drops. Such tiny drops can be separated from the big droplets via centrifugation. Both the large and small particles could be sufficiently mono-dispersed to prepare articles such as optical band gap materials.

Preparation of Rods

Selective withdrawal can also be used to form particles in shapes other than spherical. Small mono-dispersed rods can be formed by illuminating the thin stream containing the pre-polymer with the polymerizing light before the stream breaks up into droplets. The stream may be polymerized into a rod having the width of the stream, but having a length dependent upon the length over which the stream has been exposed to the light. When the stream breaks up into droplets, the rods will remain intact and the breakup will occur between the places where the stream has been exposed to the polymerizing radiation. This length can be varied by exposing the stream over a variable width for a very short period of time, or by exposing a narrow portion of the stream for a varying amounts of time. By repetitively turning the UV light on and off, many particles can be formed.

Combinatorial Synthesis

The selective withdrawal method generates droplets of one fluid that are contained within a second fluid. These droplets can serve as vessels in which reactions are carried out with confinement of the products. When the composition of reactants in the lower phase from which fluid is drawn is caused to vary with time, the resulting droplets will also vary in composition. This property can be utilized for the combinatorial synthesis of polymers and molecules, and the subsequent selection of products having a desired set of properties.

In one prospective example of this method, a luminescent polymer that is prepared from three precursors can be optimized for the ratio of the three components that gives polymer with a specific energy of excitation or emission. In one mode, the lower phase from which the solution is withdrawn contains the three components and can also be exchanged with a flowing solution. If during the selective withdrawal the composition of the lower phase is varied, then the droplets generated from this phase have a varied composition that is determined by the composition of the lower phase. By varying the concentration of one component while holding the other two components at constant concentration, the dependence of polymer properties on the concentration of that precursor can be optimized. As the droplets flow through the tube, they are maintained in the order that reflects the relative compositions. In this example, the droplets can be passed by a light source or heat source to effect reaction or polymerization and then passed by a spectrophotometer or fluorimeter to determine properties. This example can be extended to the preparation of libraries of many other functional polymers and to the preparation of composite materials and molecules.

EXAMPLES

The following examples further illustrate the principles of the present invention. The examples are provided for purposes of illustration only, and are not to be construed as limiting the invention in any way.

Example 1

Encapsulating Poppy Seeds with PEG

A lower fluid comprising 25 ml of a pre-polymer mixture comprising 10% (w/v) PEG, specifically poly(ethyleneglycol)-bisphenol A diglycidyl ether tetraacrylate, available from Polysciences Inc., in heavy water (deuterium oxide), was added to a 500 ml beaker. This fluid had a density of about 1.1 g/cc and a viscosity between about 1 and 50 cSt (centi-Stokes). The articles to be encapsulated, poppy seeds, were mixed into the PEG/water solution, along with Polyfluor 512 fluorescent dye, available from Polysciences, Inc. The poppy seeds were generally kidney-shaped, and had a long-axis dimension of approximately 800 microns. 400 ml of Heavy Mineral Oil, available from Fisher Scientific, was added to the beaker to comprise the upper fluid layer. This oil had a density of about 0.87 g/cc and a viscosity of about 200 cSt. The surface tension at the interface of the fluid layers was approximately 30 dyn/cm.

A plastic pipette having an inner diameter of about 0.5 cm was connected to a length of Tygon tubing, the other end of which was connected to a rotary gear pump designed for constant flow. The orifice of the tube was arranged at a height of approximately 1 cm above the interface of the oil and the PEG/water mixture. The pump was a Tuthill Mag Drive rotary gear pump, which delivered about 0.11 ml/rev., and withdrew fluid at a rate of about 10 ml/sec. Special care was taken to prevent the particles from passing completely through the length of tubing and entering the pump, since the pump gears would destroy the particles. In order to prevent such passage, the pump was stopped prior to entry of the particles into the pump through the Tygon tubing. The tube orifice was then moved to a collection vessel, the pump flow was reversed and the product was collected in a collection vessel.

The PEG was polymerized by adding ethyl eosin to the pre-polymer mixture. Free radicals were generated by exposing the eosin/PEG mixture to light at a wavelength of 520 nm using a mercury lamp. The coated seeds were retrieved from the collection vessel and examined under a microscope to confirm the coating. Under microscopy it was confirmed that the poppy seeds were covered with a conformal polymerized coating having a thickness which appeared to be approximately 10 microns.

Example 2

Encapsulating Polystyrene Beads with PEG

The process described above was repeated utilizing spherical polystyrene beads having a diameter of approximately 200–300 microns as the particles to be coated. FIG. 3a illustrates a polystyrene bead coated with the PEG polymer. FIG. 3b shows a fluorescent image of the bead and its coat at the bead equator. The bead is not fluorescent. The coat is fluorescent, and appears as a uniform white ring around the dark bead. In this case, the bead diameter was about 200 microns and the coating on the bead appeared to have a thickness of approximately 20 microns.

Example 3

Encapsulating Polystyrene Beads with Agarose

Figure 4B:
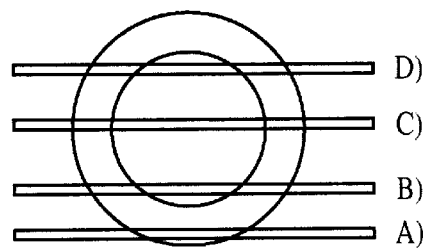
FIG. 4*b* is a schematic diagram showing a side view of the bead and coat along with the corresponding sample slices of FIG. 4*a*.

In this example, the lower fluid comprised Low Gelling Temperature Agarose type VII, available from Sigma-Aldrich. The rigidity of the agarose depends on the temperature. At high temperatures (around 70° C.) the agarose is a liquid. At low temperatures (0° C.) the agarose is rigid. 25 ml of 5% agarose/heavy water mixture was added to a 500 ml beaker. The beaker was maintained at 70° C. by an external water bath. The polystyrene beads were added to the beaker, along with Polyfluor 512 fluorescent dye. The beaker was then filled with Heavy Mineral Oil, which was preheated to 70° C. The particles were then coated using the technique described in the preceding Example. In this case, the collection vessel was maintained in ice water. The coated beads were retrieved from the collection vessel and examined under a confocal microscope. A 3-D image was constructed, and the coating was confirmed. The images are shown in FIG. 4a. These images represent horizontal slices of the bead and coat which are vertically separated by 22 microns. FIG. 4b is a schematic diagram showing a side view of the bead and coat along with the four sample slices. The corresponding slices are marked in the confocal image. Since the bead is opaque, it was only possible to image the bottom half of the bead. The confocal microscopy images show that the beads have a uniform coat, which coat appeared to have a thickness of about 10 microns.

What is claimed is:

1. A method for encapsulating particles, the method comprising:

providing a container having two liquids therein, said liquids having different densities and being substantially immiscible relative to each other and being situated in said container such that an interface exists between the liquids, the liquid of lesser density comprising an upper liquid and the liquid of greater density comprising a lower liquid, the lower liquid comprising a coating liquid and having said particles to be coated entrained therein, the upper liquid having a greater viscosity than the lower liquid;

inserting a tube having an orifice into the container such that said orifice is positioned in the upper liquid above said interface, said tube being operably connected to a pump for withdrawing liquid from the container;

activating said pump and establishing a pumping rate sufficient to form a spout extending between said interface and said orifice of said tube, said spout substantially comprising said lower liquid being withdrawn from said container, said spout having a maximum diameter base portion at said interface and decreasing in diameter as the spout approaches said tube, said base portion diameter being greater than the diameters of the particles to be coated, said pumping rate being sufficient to draw said particles from said lower liquid and through the spout;

coating a particle by drawing the particle upwardly through said spout from said base portion wherein the particle is engulfed by a coating of said spout liquid, to an upper spout portion, said upper spout portion having a diameter less than the diameter of the particle, thereby causing a break in said spout and freeing said coated particle for flow through said tube;

re-establishing said spout by continuing said pumping at said sufficient pumping rate, and coating additional particles by drawing each particle to be coated upwardly through said spout from said base portion to an upper portion of said re-established spout having a diameter less than the diameter of the particle being coated, thereby causing a break in said spout and freeing said coated particle;

repeating said coating process until all of said particles to be coated have been drawn upwardly through said spout and coated with said spout liquid; and collecting said coated particles.

2. The method of claim 1, wherein said coating liquid comprises a pre-polymer liquid.

3. The method of claim 2, further comprising, after the step of coating one of the particles, polymerizing said pre-polymer liquid, and cross-linking said polymerized coating into a hard coat.

4. The method of claim 3, wherein said polymerized coating is cross-linked by shining an ultraviolet light on the coating.

5. The method of claim 3, wherein said polymerized coating is cross-linked by passing the polymer through a temperature gradient.

6. The method of claim 3, wherein said polymerized coating is cross-linked by a chemical initiation reaction.

7. The method of claim 1, wherein said tube comprises a pipette having an inner diameter of about 0.5 cm.

8. The method of claim 1, wherein said upper fluid comprises an oil having a viscosity of about 200 centi-Stokes.

9. The method of claim 1, wherein the lower liquid comprises a solution of poly(ethylene glycol) having a viscosity between about 1 and 50 centi-Stokes.

10. The method of claim 1, wherein said particles to be coated have a diameter between about 100 and 800 microns.

11. The method of claim 1, wherein said particles to be coated have a diameter between about 100 and 300 microns.

12. The method of claim 11, wherein said particles to be coated have a diameter of approximately 200 microns, and wherein the coating conforms to the size and shape of the particle and has a thickness of approximately 10–15 microns.

13. The method of claim 1, wherein a plurality of tubes are inserted into the upper liquid, each of said tubes being operably connected to a pump for withdrawing liquid from the container and for coating particles drawn through each of said tubes.

14. The method of claim 1, wherein a plurality of tubes are inserted into the upper liquid, each of said tubes being operably connected to a separate pump for withdrawing liquid from the container and for coating particles drawn through said tube.

15. The method of claim 1, wherein the particle is a cell.

16. The method of claim 15, wherein the cell is an islet cell.

17. A coated islet cell encapsulated by the method of claim 1, wherein the islet cell has an outer coating of uniform thickness that conforms to the size and shape of the cell.

18. The coated islet cell of claim 17, wherein the outer coating has a thickness of about 10–15 microns.

19. A method of treating a patient with diabetes comprising administering a pharmaceutically effective amount of the coated islet cell of claim 17.

20. A method of providing a therapeutic compound to a patient comprising administering a pharmaceutically effective amount of a coated particle encapsulated by the method of claim 1.

* * * * *